(12) United States Patent
Polliack et al.

(10) Patent No.: US 8,920,351 B2
(45) Date of Patent: *Dec. 30, 2014

(54) EMERGENCY STABILIZATION OF A FRACTURED PELVIS OR AN INJURED NECK

(75) Inventors: Adrian Abram Polliack, Lake Oswego, OR (US); Lance David Hopman, Tigard, OR (US); Lane Michael Johnson, Tualatin, OR (US); Mark Douglas Smith, Damascus, OR (US)

(73) Assignee: The Seaberg Company, Inc., Wilsonville, OR (US)

( * ) Notice: Subject to any disclaimer, the term of this patent is extended or adjusted under 35 U.S.C. 154(b) by 365 days.

This patent is subject to a terminal disclaimer.

(21) Appl. No.: 13/489,277

(22) Filed: Jun. 5, 2012

(65) Prior Publication Data

US 2012/0245500 A1 Sep. 27, 2012

Related U.S. Application Data

(63) Continuation-in-part of application No. 12/462,754, filed on Aug. 7, 2009, now Pat. No. 8,192,383.

(51) Int. Cl.
*A61F 5/00* (2006.01)
*A61F 5/24* (2006.01)
*A41F 9/00* (2006.01)
*A61F 5/058* (2006.01)

(52) U.S. Cl.
CPC ......... *A61F 5/05825* (2013.01); *A61F 5/05883* (2013.01)
USPC .................................. 602/19; 128/96.1; 2/311

(58) Field of Classification Search
USPC ............. 602/19, 36, 5, 23–24, 32, 38–39, 60, 602/67–68; 128/96.1, 98.1, 99.1, 100.1, 128/101.1, 869, 876; 2/311–324, 309; 24/68 R, 585, 31 R, 32, 33, 36, 578.15, 24/579.09; 601/71, 124

See application file for complete search history.

(56) References Cited

U.S. PATENT DOCUMENTS

| 2,344,021 A | 3/1944 | Bouziane |
|---|---|---|
| 2,554,337 A | 5/1951 | Lampert |

(Continued)

FOREIGN PATENT DOCUMENTS

| DE | 20300739 | 5/2003 |
|---|---|---|
| EP | 0462088 | 12/1991 |

(Continued)

OTHER PUBLICATIONS

Ambu—Photos of Cervical Collar 4 pages, prior to May 2012.

(Continued)

*Primary Examiner* — Alireza Nia
*Assistant Examiner* — Tarla Patel
(74) *Attorney, Agent, or Firm* — Chernoff, Vilhauer, McClung & Stenzel, LLP

(57) ABSTRACT

A hip-girdling pelvic sling device for maintaining a desired amount of tension surrounding a person's hips and pelvis to securely support and stabilize a pelvis that has been fractured. Areas of mating types of fastener material such as mating hook-bearing fastener material and loop pile fastener material are arranged on the device to enable a strap to be secured at various effective lengths to provide a wide range of adjustability. The device may include inflatable bladders, stays, and a chin support and may be wrapped around a patient's neck as a cervical support collar.

10 Claims, 12 Drawing Sheets

(56) References Cited

U.S. PATENT DOCUMENTS

| | | |
|---|---|---|
| 3,171,410 A | 3/1965 | Towle, Jr. et al. |
| 3,594,872 A | 7/1971 | Kulwin et al. |
| 3,933,150 A | 1/1976 | Kaplan et al. |
| 4,049,854 A | 9/1977 | Casey et al. |
| 4,175,562 A | 11/1979 | Honan |
| 4,233,980 A | 11/1980 | McRae et al. |
| 4,390,014 A | 6/1983 | Forman |
| 4,459,979 A | 7/1984 | Lewis, Jr. |
| 4,545,370 A | 10/1985 | Welsh |
| 4,577,622 A | 3/1986 | Jennings |
| 4,580,555 A | 4/1986 | Coppess |
| 4,715,364 A | 12/1987 | Noguchi |
| 4,928,674 A | 5/1990 | Halperin et al. |
| 4,964,401 A | 10/1990 | Taigen |
| 4,991,573 A | 2/1991 | Miller |
| 5,086,759 A | 2/1992 | Buddingh |
| 5,234,459 A | 8/1993 | Lee |
| 5,307,521 A | 5/1994 | Davis |
| 5,307,811 A | 5/1994 | Sigwart et al. |
| 5,338,239 A | 8/1994 | Cleaveland |
| 5,383,893 A | 1/1995 | Daneshvar |
| 5,383,920 A | 1/1995 | Sikes |
| 5,403,266 A * | 4/1995 | Bragg et al. ............. 602/5 |
| 5,407,422 A | 4/1995 | Matthijs et al. |
| 5,433,724 A | 7/1995 | Kawasaki et al. |
| 5,486,194 A | 1/1996 | Kawasaki et al. |
| 5,489,260 A | 2/1996 | Striano |
| 5,500,959 A | 3/1996 | Yewer, Jr. |
| 5,542,427 A | 8/1996 | Akerfeldt |
| 5,551,085 A | 9/1996 | Leighton |
| 5,643,315 A | 7/1997 | Daneshvar |
| 5,695,453 A | 12/1997 | Neal |
| 5,707,177 A | 1/1998 | Lehrer et al. |
| 5,741,295 A | 4/1998 | McEwen |
| 5,743,864 A | 4/1998 | Baldwin, II |
| 5,785,671 A | 7/1998 | Striano |
| 5,788,658 A | 8/1998 | Islava |
| 5,792,173 A | 8/1998 | Breen et al. |
| 5,799,650 A | 9/1998 | Harris |
| 5,830,168 A | 11/1998 | Finnell et al. |
| 5,893,368 A | 4/1999 | Sugerman |
| 5,968,072 A | 10/1999 | Hite et al. |
| 5,997,564 A | 12/1999 | Shehata et al. |
| 6,007,559 A | 12/1999 | Arkans |
| 6,053,883 A | 4/2000 | Schiek, Sr. |
| 6,065,166 A | 5/2000 | Sharrock et al. |
| 6,066,109 A | 5/2000 | Buser et al. |
| 6,165,147 A | 12/2000 | Morrow |
| 6,179,796 B1 | 1/2001 | Waldridge |
| 6,240,923 B1 | 6/2001 | Barrick |
| 6,264,673 B1 | 7/2001 | Egnelov |
| 6,352,074 B1 | 3/2002 | Okada |
| 6,503,217 B1 | 1/2003 | Gibbs et al. |
| 6,503,266 B1 | 1/2003 | Sjogren et al. |
| 6,554,784 B1 | 4/2003 | Krieg et al. |
| 6,610,022 B1 | 8/2003 | Ashbaugh et al. |
| 6,616,620 B2 | 9/2003 | Sherman et al. |
| 6,626,856 B2 | 9/2003 | Manoach |
| 6,939,314 B2 | 9/2005 | Hall |
| 7,008,389 B2 | 3/2006 | Krieg et al. |
| 7,094,213 B1 | 8/2006 | Cook |
| 7,329,792 B2 | 2/2008 | Buckman et al. |
| 7,574,761 B2 | 8/2009 | Davis |
| 7,677,605 B2 | 3/2010 | Cook |
| 7,931,607 B2 | 4/2011 | Biondo et al. |
| 8,142,378 B2 | 3/2012 | Reis et al. |
| 8,192,383 B2 * | 6/2012 | Polliack et al. ............. 602/19 |
| 2001/0053884 A1 | 12/2001 | Krieg et al. |
| 2002/0068890 A1 | 6/2002 | Schwenn et al. |
| 2002/0144343 A1 | 10/2002 | Kuiper et al. |
| 2002/0169401 A1 | 11/2002 | Walpin |
| 2003/0176825 A1 | 9/2003 | Yavnai |
| 2005/0283102 A1 * | 12/2005 | Schwenn et al. ............. 602/5 |
| 2006/0135898 A1 | 6/2006 | Richardson |
| 2006/0206992 A1 | 9/2006 | Godshaw et al. |
| 2007/0117479 A1 | 5/2007 | Weinel et al. |
| 2007/0282230 A1 | 12/2007 | Valderrabano et al. |
| 2008/0004555 A1 | 1/2008 | Reis et al. |
| 2008/0251087 A1 | 10/2008 | Richardson |
| 2008/0281351 A1 | 11/2008 | Croushorn et al. |
| 2010/0100120 A1 | 4/2010 | Perkins et al. |
| 2010/0152770 A1 | 6/2010 | Spencer |
| 2010/0179586 A1 | 7/2010 | Ward et al. |
| 2010/0298748 A1 * | 11/2010 | Rosenfeld et al. ............. 602/17 |
| 2011/0034845 A1 | 2/2011 | Polliack et al. |
| 2013/0324898 A1 * | 12/2013 | Polliack et al. ............. 602/18 |

FOREIGN PATENT DOCUMENTS

| | | |
|---|---|---|
| KR | 900005852 B1 | 8/1990 |
| WO | 9405221 | 3/1994 |
| WO | 9702783 | 1/1997 |
| WO | 0045756 A1 | 8/2000 |
| WO | 0189433 A1 | 11/2001 |
| WO | 03005743 A2 | 9/2003 |
| WO | 2011016824 A2 | 2/2011 |

OTHER PUBLICATIONS

PYNG Medical T-Pod Pelvic Stabilization Device Instruction Sheet single page, prior to May 2012.

Blackbourne, Joseph Lister, Noncompressible Arterial Hemorrhage, and the Next Generation of "Tourniquets"?, article in Jan.-Mar. 2008 issue, PB 8-08-1/2/3, AMEDD Journal, US Army Medical Dept. Fort Sam Houston, TX, 6 pgs.

Kinzel, Development of a Field Packable Junctional Tourniquet, Jan. 2, 2011, MilTech, Bozeman, MT, 16 pages.

Kragh, New Tourniquet Device Concepts for Battlefield Hemorrhage Control, Apr.-Jun. 2011 issue; The Army Medical Dept. Journal, pp. 38-47.

Seaberg Company, Int'l Search Report, PCT/US10/001682, Mar. 15, 2011, 5 pages.

Seaberg Company, Int'l Written Opinion, PCT/US10/001682, Mar. 15, 2011, 4 pages.

Seaberg Company, Int'l Search Report, PCT/US12/50437, Dec. 31, 2012, 16 pages.

Seaberg Company, European Search Report, EP10806730.7-2310, Jan. 10, 2013, 5 pages.

* cited by examiner

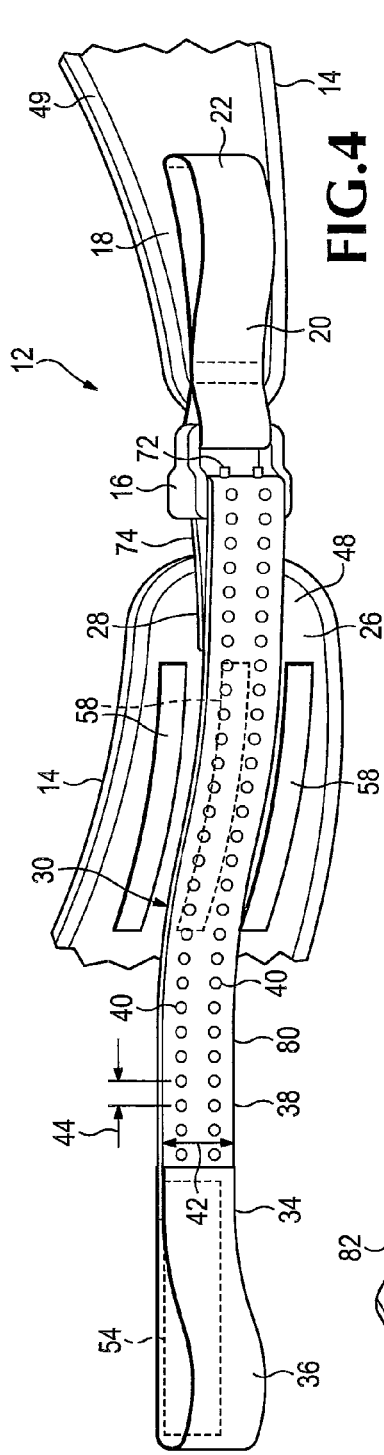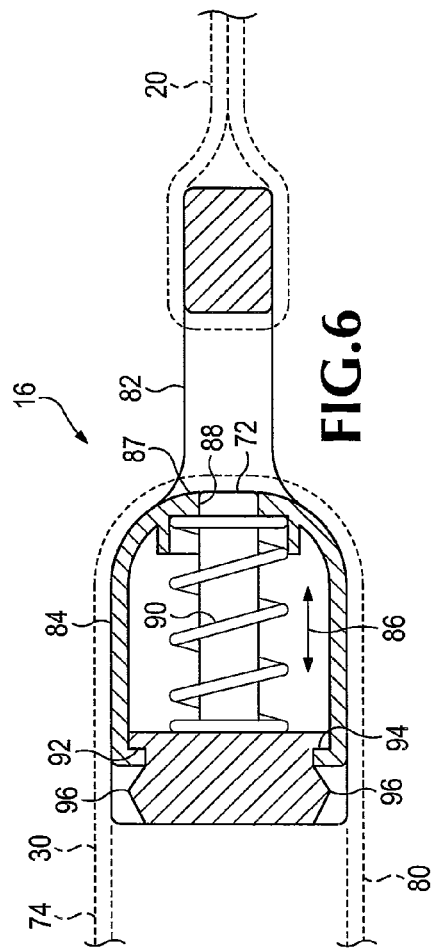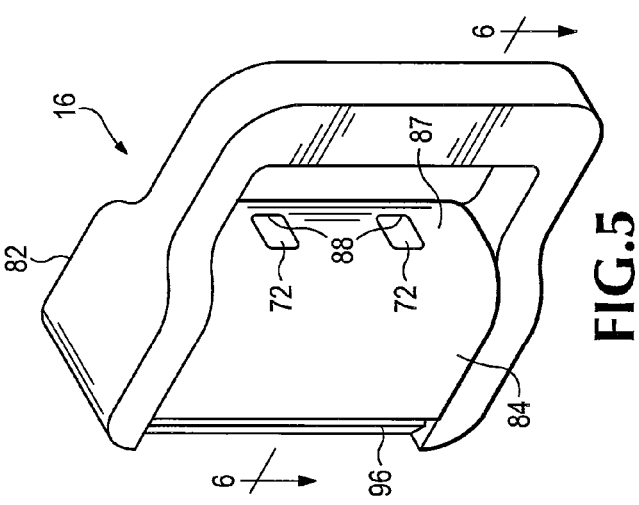

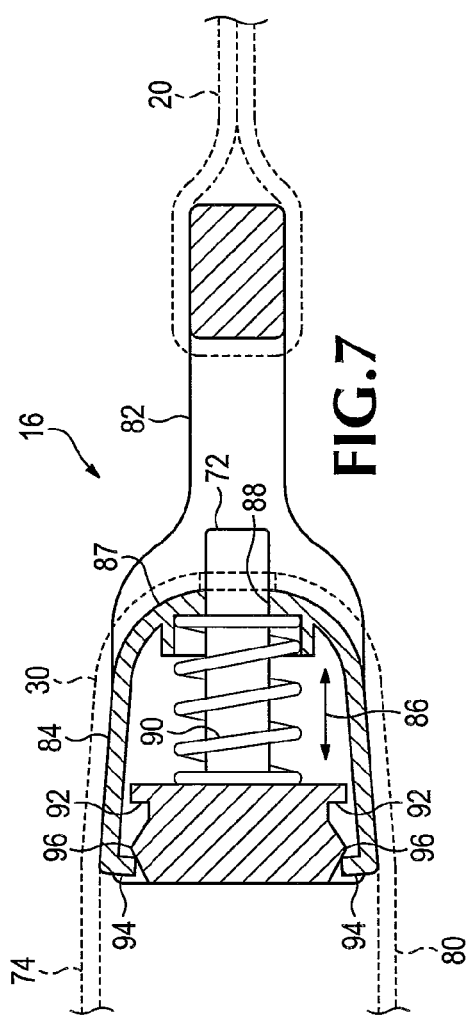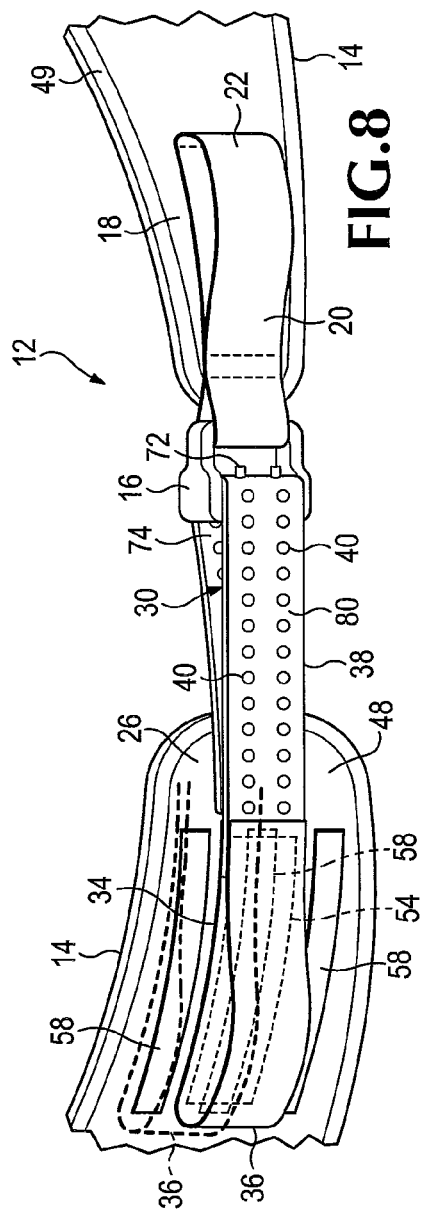

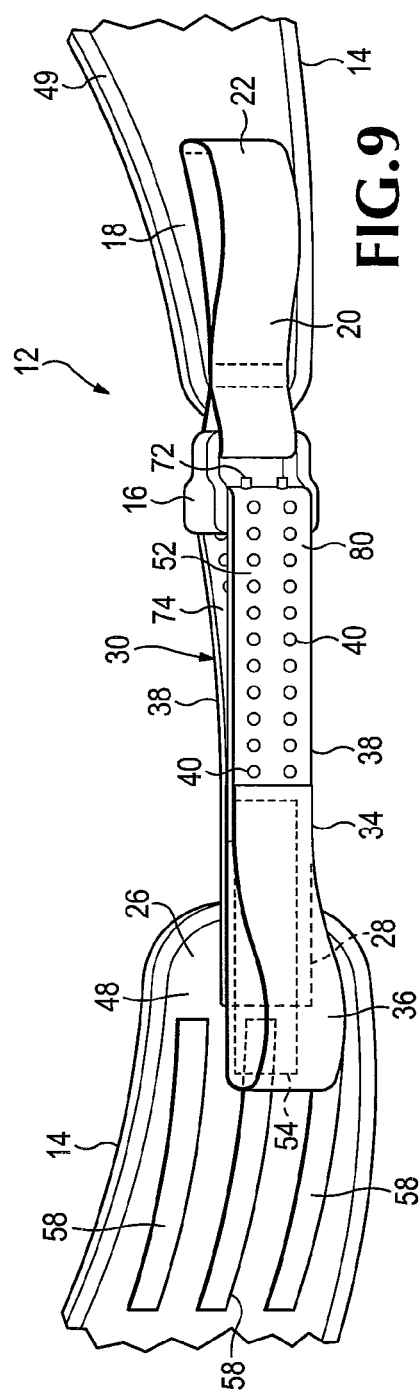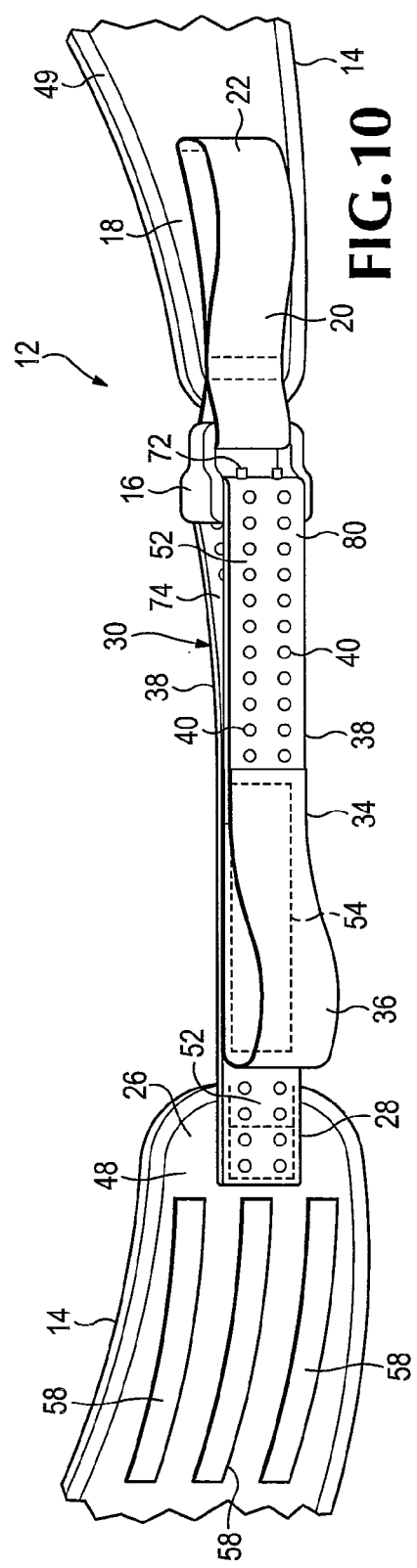

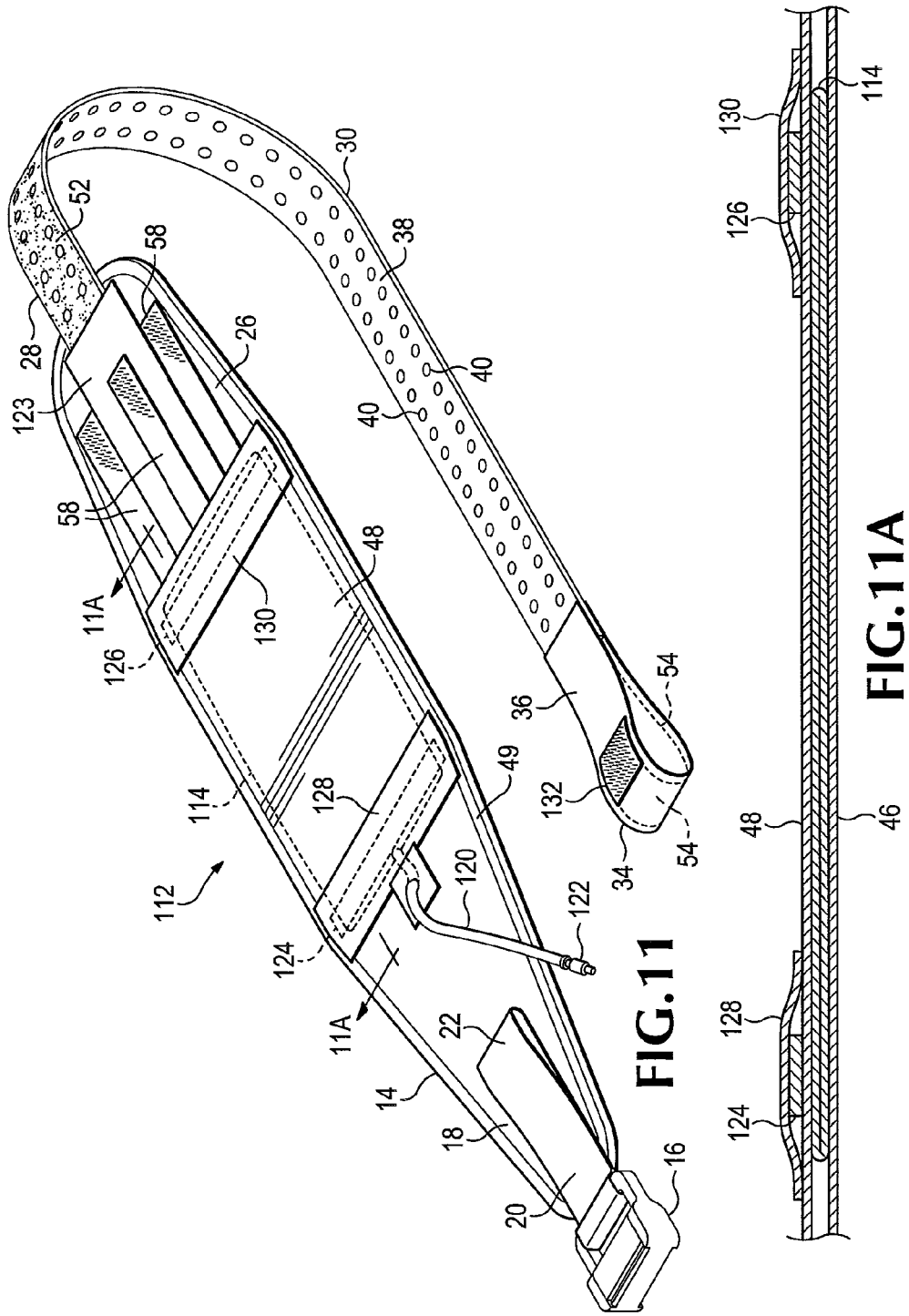

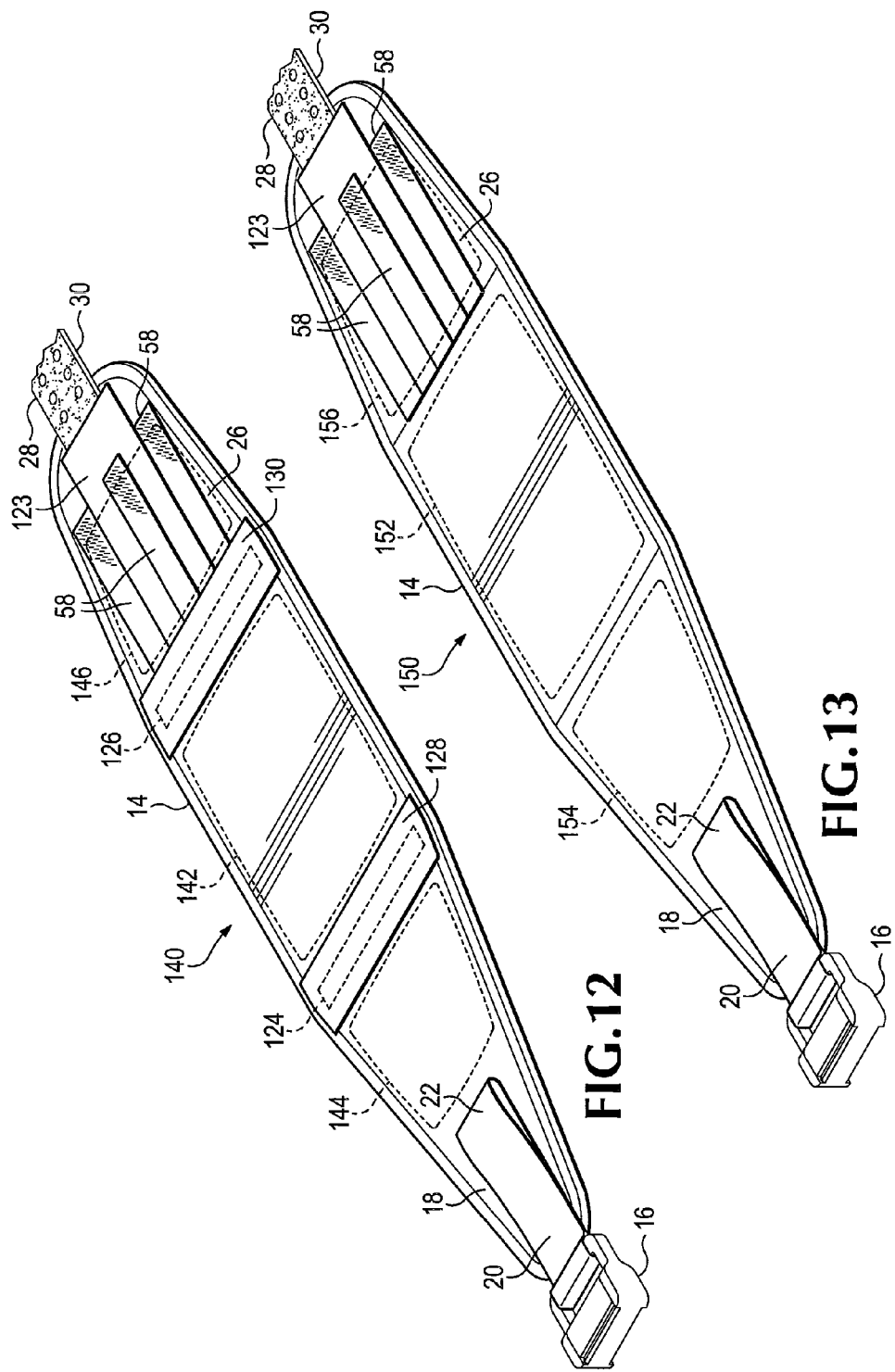

EMERGENCY STABILIZATION OF A FRACTURED PELVIS OR AN INJURED NECK

CROSS-REFERENCE TO RELATED APPLICATIONS

This application is a continuation-in-part of U.S. patent application Ser. No. 12/462,754 filed Aug. 7, 2009, now U.S. Pat. No. 8,192,383.

BACKGROUND OF THE INVENTION

The present invention relates to emergency treatment of a fractured pelvis or an injured neck. In particular, the invention provides a device and a method for its use in a closed reduction of a fracture of a pelvis and for stabilizing the fractured pelvis pending further treatment, and which may also be used as a cervical support collar.

Internal bleeding due to a fractured pelvis can easily result in death. Rapidly reducing a fracture of a pelvis decreases mortality substantially, and devices are known for reducing a fracture and stabilizing the fractured pelvis in emergency situations, so that a patient can be transported to a hospital or other treatment facility. Stabilization of the pelvis within the first hour after a fracture occurs is critical and may often determine whether the patient lives or dies.

Krieg, et al., U.S. Pat. Nos. 6,554,784 and 7,008,389 disclose devices which can be used to encircle the hips of an injured person and provide a proper amount of hoop tension to urge the parts of a person's fractured pelvic ring toward a normal relationship and thus reduce internal bleeding at the site or sites of fracture. The devices disclosed by Krieg, et al., provide for non-invasive reduction of a fractured pelvis and for stabilization of the person's pelvis during transport to a hospital or other medical facility where a fractured pelvis can be surgically repaired. The Krieg, et al., devices are particularly appropriate for use in emergency situations such as the scene of a car accident, a skiing accident, a mountain-climbing accident, or industrial injury, for example.

In a commercially available embodiment of a Krieg, et al., device, a broad belt-like body partially encircles the patient's hip region, and a strap adjustably interconnects the opposite ends of the body of the device. A special buckle is attached to one end of the body of the device, and a strap extends between the buckle and a strap mounting piece that must be fastened to the opposite end of the main body at a location that must be selected when using the device on an injured person, although proper placement of the strap mounting piece is not intuitively obvious to an untrained person. The strap, extending through the buckle, must then be pulled to provide hoop tension to support the pelvis. The special buckle senses the correct amount of tension, at which it engages the strap, preventing over tightening. A relatively small range of adjustability of the circumference of the device is available, however, with the strap mounting piece in a particular location. As a result the strap mounting piece may need to be relocated on the main body before sufficient tension can be obtained and retained by the buckle.

Because of the provision of the strap and its mounting piece as a separate, removable, part of the device, application of the device involves several steps, so proper training and familiarity with the device can be critical to its effective use. Also, the removability of the strap requires a well-trained person to rearrange the parts of the device properly for reuse once it has been used on an injured person.

In order to avoid the expenditure of time required to determine where to attach the strap mounting piece to the main body of such a device, and to simplify effective application, an improved device for use by emergency medical aid providers is desired, capable of stabilizing a pelvis, in which such placement of a strap mounting member onto the main body of the device is not necessary, yet ample adjustability is immediately available. Ideally, such a device could also have additional utility, as well.

SUMMARY OF THE INVENTION

The present invention, as defined by the claims which form a part of the disclosure herein, provides an answer to the aforementioned need for a simplified device for encircling a pelvis that has been fractured, reducing the fracture, and stabilizing the pelvis by providing a proper amount of encircling tension.

As a first aspect of a device as disclosed herein, a wide belt-like main body of a device for stabilizing a fractured pelvis has a pair of opposite end portions, one of which carries a buckle, and the other of which has an inner end of a strap member attached thereto. The strap member is arranged to extend through the buckle and to be doubled back to extend toward the end of the main body to which its inner end is attached. Fastener material is present in locations providing a wide range of adjustment of the effective lengths to provide a wide range of adjustability.

In one embodiment of the device disclosed herein, fastening material such as Velcro™ hook-bearing fastener material is provided on an outer end portion of the strap, and material such as Velcro™ loop-bearing fastener material is provided along an intermediate portion of the strap.

In one embodiment of the device, a surface of the main body of the device at the end from which the strap extends is securely and matingly receptive to hook-bearing fastener material such as Velcro™ hook-bearing fastener material located on the outer end portion of the strap.

In one embodiment of the device disclosed herein, material of much of the outer face of the end portion of the main body of the device is receptive to fastener material of the Velcro™ hook-bearing type, and an area of hook-bearing fastener material of the Velcro™ type is also located on the end portion, where it can engage and grip the loop-bearing fastener material on the intermediate portion of the strap when the strap is doubled back alongside itself and pulled through the buckle far enough for the device to fit around the pelvic area of a relatively slender injured person with the necessary amount of tension.

In one embodiment of the device disclosed herein the strap is provided with hook-bearing fastener material located where it can be used to secure the outer end portion of the strap to an intermediate portion of the strap with the device wrapped around a patient's neck as a cervical support collar.

In one embodiment of the device disclosed herein one or more inflatable bladders may be included in the main body, to provide additional support for a patient when the device is in use, either as a pelvis-stabilizing device or as a cervical support collar around a patient's neck.

In one embodiment the device may include a chin receptacle or chin rest at one end of the main body, to be available for use of the device as a cervical collar to support a person's neck.

In one embodiment of the device disclosed herein a pair of elongate stays may be included in the main body of the device, spaced apart from each other and extending transversely of the length of the main body portion so as to provide additional support for a person's neck when the device is used as a cervical support collar.

A method disclosed herein includes supporting a persons neck by providing a wide belt-like main body of fabric with a strap extending from one end and which has a chin receptacle associated with a margin at the opposite end, wrapping the belt-like main body portion around a person's neck, supporting the chin in the receptacle, and securing the end of the strap. One embodiment of the method includes the step of placing a chin rest in a deployed position.

The foregoing and other features of the invention will be more readily understood upon consideration of the following detailed description of the invention taken in conjunction with the accompanying drawings.

BRIEF DESCRIPTION OF THE SEVERAL DRAWINGS

FIG. 4 is an isometric front view of end portions of the main body of the pelvis-stabilizing device shown in FIGS. 1-3, illustrating the device secured and under tension at a small circumference, as if to fit a slender person.

FIG. 5 is an isometric view of a buckle useful as a part of the pelvis-stabilizing device shown in FIGS. 1-4.

FIG. 6 is a sectional view of the buckle shown in FIG. 5, taken along line 6-6 of FIG. 5, with the buckle in a relaxed condition.

FIG. 7 is a view similar to FIG. 6, but showing the condition of the buckle when subjected to a predetermined tension to cause the buckle to engage a strap that is a part of the pelvis-stabilizing device shown in FIGS. 1-4.

FIG. 8 is a view similar to FIG. 4 showing the pelvis-stabilizing and supporting device under tension so that the buckle engages the strap, at a larger circumference than that shown in FIG. 4, as if properly in place on a larger person.

FIG. 9 is a view similar to FIG. 8, showing the pelvis-stabilizing and supporting device with the strap under tension and engaged by the belt at yet a larger circumference than that shown in FIG. 8, as if properly secured in place on a yet larger person.

FIG. 10 is a view similar to FIG. 9, showing the pelvis-stabilizing and supporting device with the strap under tension and engaged by the buckle as if properly secured in place around a person of yet larger circumference, near the maximum for the size of the device.

FIG. 11 is an isometric view of an alternative embodiment of the pelvis-stabilizing device shown in FIGS. 1-10, which may also be used as a cervical collar for the protection of a person's neck.

FIG. 11A is a sectional view taken along line A-A in FIG. 11.

FIG. 12 is an isometric view of the main body portion of a pelvis-stabilizing device which is another alternative embodiment of the device shown in FIGS. 1-10.

FIG. 13 is an isometric view of the main body portion of a pelvis-stabilizing device which is yet a further alternative embodiment of the device shown in FIGS. 1-10.

DETAILED DESCRIPTION OF EMBODIMENTS

Figure 1:
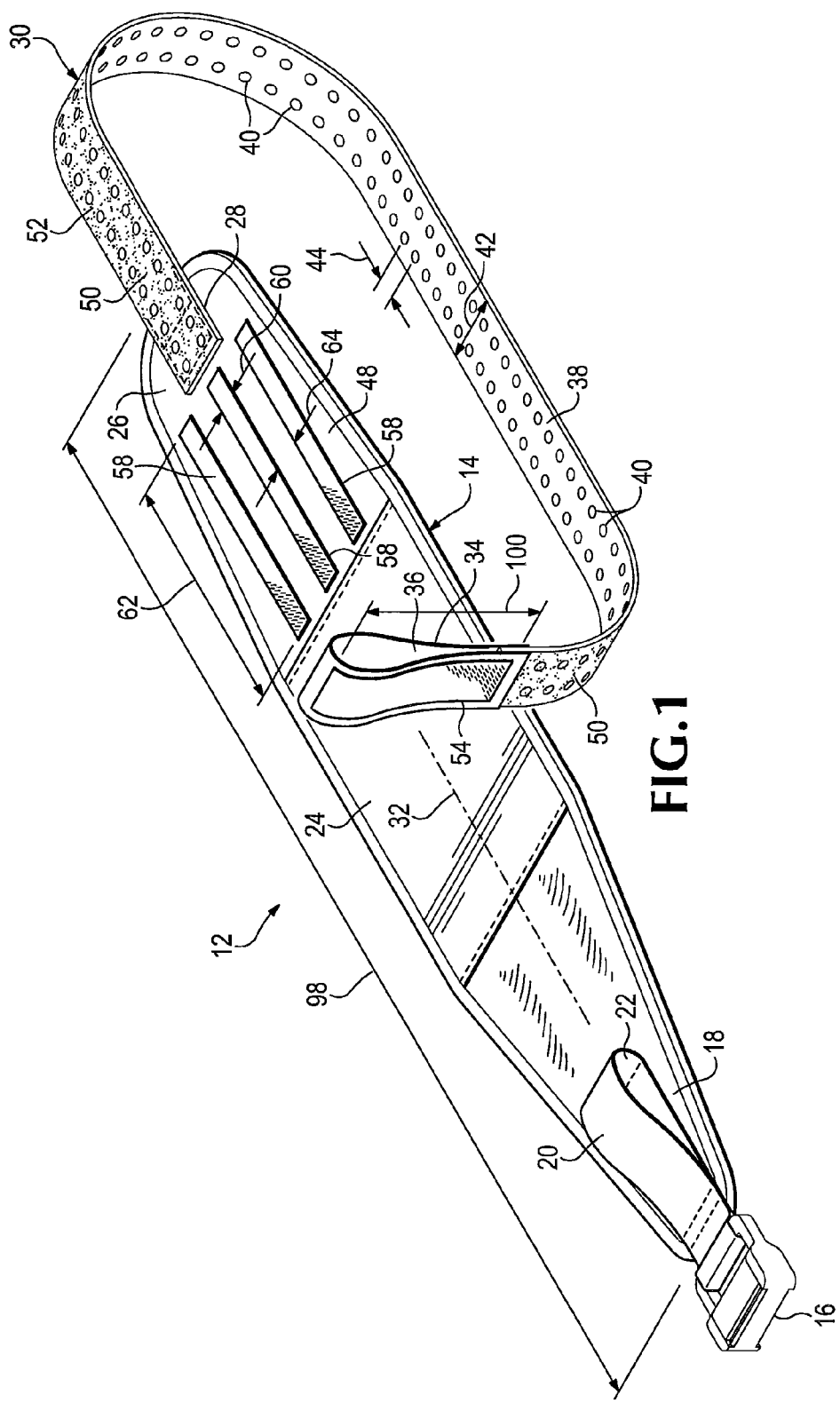
FIG. 1 is an isometric view of a pelvis-stabilizing device that is an exemplary embodiment of an aspect of the present invention.

Referring first to FIGS. 1-4 of the drawings which form a part of the disclosure herein, a pelvis supporting and stabilizing device 12 for stabilizing a fractured pelvis, hereinafter often called a pelvic sling, is shown in FIG. 1 ready for application to a person to provide stabilization and support for a fractured pelvic ring by encircling the hip region of a person. A main body portion 14 is of strong flexible material and has the general shape of a wide belt. A buckle 16 is attached to a first end portion 18 of the main body 14 by a small loop of a strap 20 of strong fabric such as woven webbing, permanently attached to the first end portion 18, as by being sewn securely to it. As used herein the term "permanently attached" means that removal and reattachment are not easily accomplished by a user and cannot be accomplished readily without use of equipment such as that needed for initial manufacture. The fabric of the strap 20 also defines a large loop 22, attached to the first end portion 18 so that it can be used as a handle by a person applying the pelvic sling 12 to an injured person, as will be explained more fully presently.

A central portion of the main body 14 may be covered on an exterior face by a sheet 24 of low friction flexible plastic material which will be exposed on the posterior side of a person on whom the pelvic sling 12 is in use, facilitating movement of such person on a backboard or other support.

At a second end portion 26, opposite the first end portion 18, an inner end 28 of an elongate flexible strap 30 is permanently attached to the main body 14, as by being sewn, riveted, or thermally or sonically welded securely to the second end portion 26 of the main body 14. The strap 30 extends longitudinally away from the second end portion 26, generally aligned with the longitudinal axis 32 of the main body 14. An outer end portion 34 of the strap 30 may include a loop 36 of strong fabric such as Nylon webbing attached to an intermediate portion 38 of the strap 30, which may be of heavier and consequently slightly stiffer, yet still flexible, webbing. The loop 36 may be securely sewn or otherwise permanently attached to the intermediate portion 38 of the strap 30. The loop 36 is thus available for use as a handle to pull the strap 30 away from the buckle 16, as will be explained more fully presently.

Pairs of holes 40 may be defined in the intermediate portion 38 of the strap 30. The holes 40 of each pair are aligned with each other transversely across the width 42 of the strap 30 and loop 36, which may be about two inches, for example. Adjacent pairs of holes 40 may be evenly spaced apart longitudinally of the strap 30 at a pitch 44 of, for example, 0.625 inch, so as to permit the effective circumference of the pelvic sling 12 to be adjusted in increments small enough to provide a desirable amount of tension in the pelvic sling 12 encircling a person's hips to stabilize a fractured pelvis.

The main body portion 14 may be of laminated fabric, and may include a central layer of padding material (not shown), between an inner layer 46 of a comfortably soft yet strong fabric such as a Nylon tricot material, on the side of the main body 14 intended to be placed against a person, and an exterior layer 48 of a strong fabric such as a tricot material of Nylon or another synthetic material brushed to produce a nap of fiber loops that can act as a fastener material of a first kind, such as a loop-bearing fastener material capable of being engaged matingly by a fastener material of a second kind, such as a hook-bearing flexible fastener material such as that well known under the trademark Velcro. As used herein, the terms "loop-bearing fastener material" and "hook-bearing fastener material" will refer to fastener material that functions similarly to the Velcro™ combination of loop-pile fabric and "thistle-cloth" to stick removably together.

A binding 49 may be provided around the exterior margin of the main body 14, and an adhesive may also be used to keep the inner and exterior layers 46 and 48 together with the central layer.

An exterior side 50 of the intermediate portion 38 of the strap 30 may be covered by a layer of a flexible loop-bearing fastener material 52, securely attached to the strap 30, as by being sewn to the webbing. Such loop-bearing fastener material 52 ideally may be present along the entire exterior side or face 50 of the strap 30, the side that is exposed in the same general direction as the exposed face of the exterior layer 48, from a point abutting the outer end portion 34 to the second end portion 26 of the main body 14, and may be present on the inner end 28 of the strap 30.

A piece of hook-bearing fastener material 54 may be securely attached to the exterior side 50 of the outer end portion 34 of the strap 30, as by being sewn to the webbing material forming the loop 36. Thus the area hook-bearing fastener material 54 may be about against the loop-bearing fastener material 52 on the exterior side 50 of the intermediate portion 38 of the strap 30.

At least one area 58 of hook-bearing fastener material is located on the second end portion of the main body 14. Advantageously, each area 58 may be a narrow, elongate piece of hook-bearing fastener material with a width 60 less than the width 42 of the strap 30, and a length 62, extending generally parallel with the longitudinal axis 32 of the main body portion 14. Such elongate areas 58 may be separated laterally from one another by a distance 64. For example, where the width 42 of the strap 30 is two inches, the width 60 of each area 58 may be about 0.75 inch, and the distance 64 between areas 58 may be about one inch. The length 62 may be as great as can be accommodated in the second end portion 26 and thus may be, for example, in the range of about 5 inches to about 7.3 inches, depending on the size of the pelvic sling 12. As will be understood in light of subsequent explanation, the foregoing dimensions are not critical, but the relationships of the width 60 and the distance 64 with the width 42 of the strap 30 can provide significant functional advantages.

Figure 2:
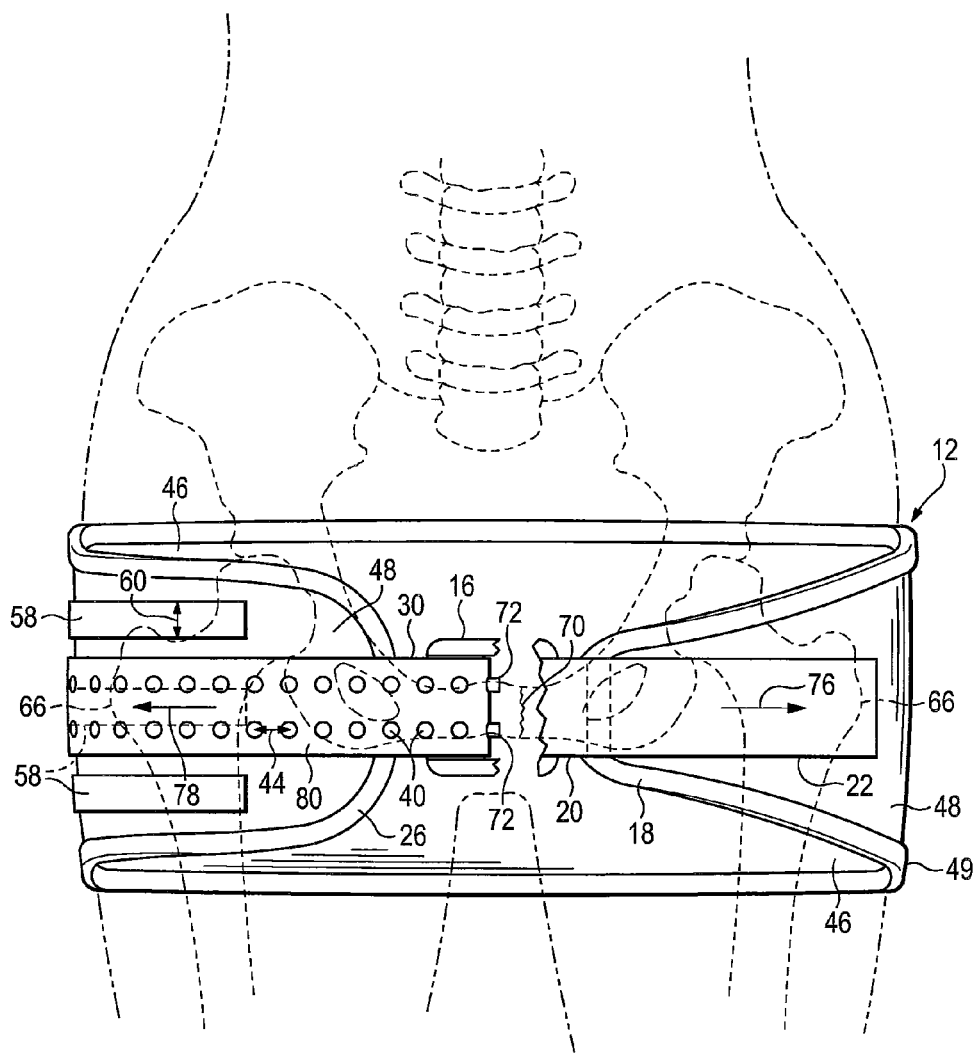
FIG. 2 is a front elevational partially cutaway view of the pelvis-stabilizing device shown in FIG. 1, showing the device extending around the pelvic area of a person and showing a portion of the skeleton of the person to illustrate the proper location of the device during use.

As may be seen in FIG. 2, when the pelvic sling 12 is properly in place on an injured person, it encircles the person's hips and buttocks at the level of the greater trochanters 66 and the symphysis pubis, with the main body portion 14 extending around the posterior of the person. The first and second ends 18 and 26 extend forward around the person's body and toward each other at the anterior side of the abdomen, with the strap 30 extending through the buckle 16 and doubled back toward the second end portion 26 of the main body portion 14, along the exterior of the pelvic sling 12. Although the pelvic sling 12 is shown consistently in one orientation herein, it is to be understood that it may be symmetrical in shape, about the central longitudinal axis 32, and thus can just as well be placed on a person with the buckle 16 and strap 30 oriented oppositely with respect to the person.

Figure 3:
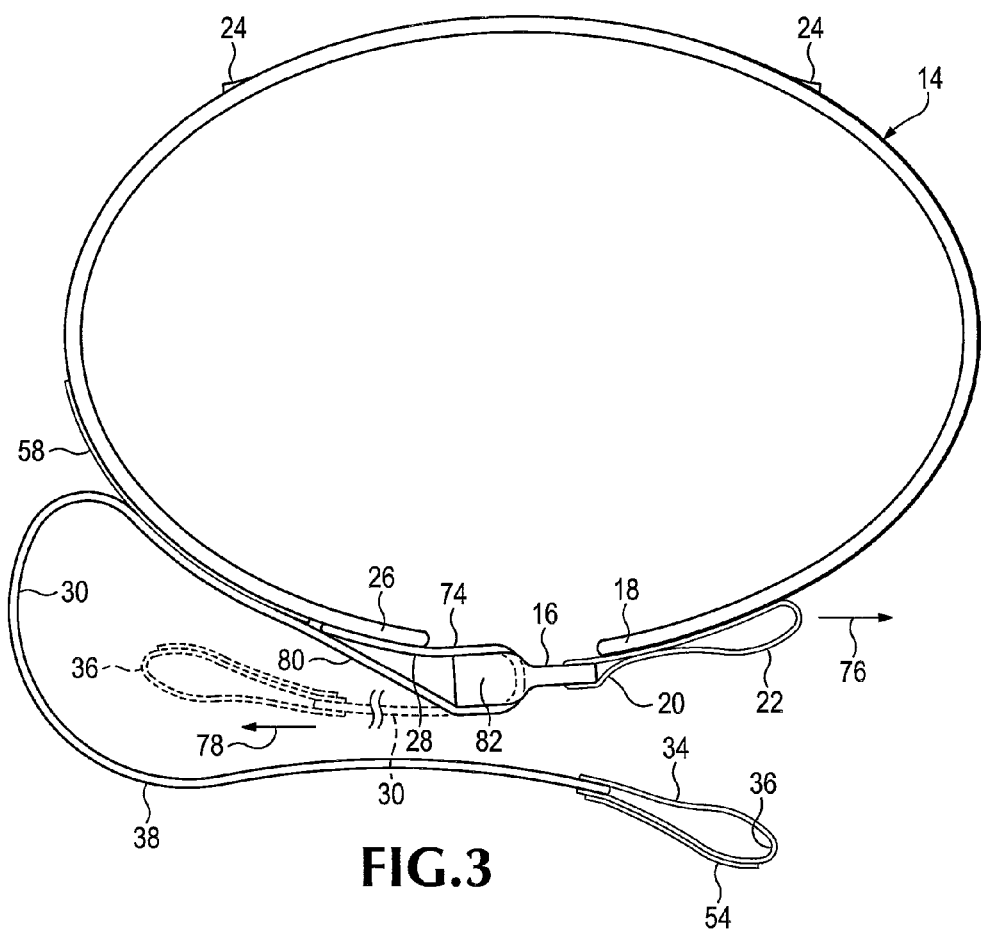
FIG. 3 is a top plan view of the pelvis-stabilizing device shown in FIGS. 1 and 2, under tension and with the strap shown secured so as to maintain tension to keep the buckle engaged while the device is fastened around a person of a minimum size for use of the device.

When the pelvic sling 12 is properly in place there is a prescribed amount of tension maintained in the main body portion 14 as it encircles the injured person, so that a fracture 70 in the pelvic ring is reduced. That is, the portions of the fractured bone are held together and stabilized by the tension in the pelvic sling 12. This tension is maintained by engagement of the buckle 16 with the strap 30. The desired amount of tension exerted on the buckle 16 by the strap 30 causes a portion of the buckle 16 to move, exposing pins 72 which extend through the ones of a pair of holes 40. As shown in FIGS. 2, 3, and 4, the outer, or pulled end, part 80 of the intermediate portion 38 of the strap 30 extends along the second end portion 26 of the main body 14, parallel with the outer surface of the exterior layer 48 when the device 12 is adjusted to a nearly minimum circumference. The loop-bearing fastener material 52 on the exterior side 50 of the strap 30 is aligned with and in mating contact with one of the areas 58 of hook-bearing fastener material, as shown in FIG. 2, so that the hook-bearing material 58 is matingly engaged with the loop-bearing fastener material 52 on the strap 30. Mating engagement of the fastener materials 58 and 52 is sufficient to maintain the tension in a portion 74 of the strap 30 between the inner end 28 and the buckle 16 to keep the pins 72 engaged in the holes 40 and thus keep the strap 30 engaged with the buckle 16.

The buckle 16 may be substantially similar to the buckle described in U.S. Pat. No. 7,008,389. Thus, as shown in FIGS. 5, 6, and 7, the buckle 16 includes two main parts, a rigid frame 82 and a sliding block 84. One side of the frame 82 is secured to the first end portion 18 of the main body portion 14 by a small loop of the fabric of the strap 20. The sliding block 84 is moveable relative to the buckle frame 82 in the directions indicated by the arrow 86. The strap 30 may extend through the opening defined by the frame 82, sliding along the contact surface of the curved face 87 of the sliding block 84 when the strap 30 is pulled to tighten the pelvic sling 12 about a person's pelvis. A pair of holes 88 are defined in the sliding block 84, and the pins 72 extend into the holes 88, with their ends preferably flush with the face 87 when the buckle 16 is not in tension. When a pair of holes 40 in the strap 30 then move into alignment with the holes 88 in the sliding block 84 the sliding block 84 is moved leftward toward the position shown in FIG. 6, so that the pins 72 protrude from the holes 88 and can extend through the holes 40, thus engaging the strap 30 and preventing it from moving relative to the buckle 16, apart from any differences in size between the pins 72 and the holes 40.

FIGS. 6 and 7 show a spring 90 positioned around one of the pins 72. An identical spring 90 may be used on the other pin 72. The springs 90 are compressed significantly when the sliding block 84 is in its fully extended position, as shown in FIG. 5, so that substantial force must be applied to the buckle 16 by tension in the straps 20 and 30 before the sliding block 84 begins to move relative to the buckle frame 82. Internal springs 90 are compressed further as the sliding block 84 moves leftward toward the position shown in FIG. 6 when there is sufficient tension in the strap 30. Flanges 92 on the buckle frame 82 are engaged by lips 94 on the sliding block 84 when the sliding block 84 is in the fully extended position as shown in FIGS. 5 and 6, thus withstanding the compressive force in the springs 90.

As the sliding block 84 moves leftward toward the position shown in FIG. 2 from the position shown in FIG. 6, the lips 94 ride up and over the tops of the ramps 96 beneath the flanges 92, so that movement of the sliding block 84 may create an audible click as the sliding block 84 moves along the pins 72 and the pins extend into the holes 40, indicating to the user that the buckle 16 is engaged with the strap 30. Thereafter the inwardly directed elastic force in the sides of the sliding block 84 presses the lips 94 against the ramps 96 and helps to keep the pins 72 engaged in the holes 40, so that a slightly lower amount of tension in the portion 80 of the strap between the pins 72 and the loop 36 is sufficient to keep the sliding block in the leftwardly depressed position, once the pins 72 have become engaged in the holes 40 as shown in FIGS. 2 and 4.

As the strap 30, when the outer end 34 is pulled away from the buckle 16, passes over the curved face 87 of the sliding block, when the predetermined tension is applied to the buckle 16 by the strap 30, the sliding block 84 moves, further compressing the springs 90 and allowing the pins 72 to extend from the holes 88 and proceed through the holes 40, preventing further movement of the strap 30 around the sliding block 84. The holes 40 in the strap 30 may have a slightly larger diameter than the largest transverse dimension of the pins 72, so that engagement of the pins 72 in the holes 40 occurs easily and smoothly at the desired tension in the strap 30. Thus, as described in previously mentioned U.S. Pat. No. 7,008,389, when the proper amount of tension has been reached in the portion of the pelvic sling 12 wrapped around an injured person, the buckle 16 will engage the strap 30, and so long as tension in the pulled portion 80 of the strap 30 extending beyond the buckle 16 is not greatly reduced, the pins 72 will remain engaged in the holes 40. It will be understood that the buckle 16 could be constructed to include only one pin 72 or more than two pins 72 and that the strap 30 could be provided with compatibly located holes 40.

Once the pins 72 have engaged the holes 40, tension should be substantially maintained in the outer or pulled portion 80 of the strap 30, and the pulled portion 80 should be moved toward the person on whom the pelvic sling is being used and should be pressed against the outer end portion 26 of the main body 14 to engage the two mating kinds of fastener material with one another to retain the strap 30 at the desired location.

It would be possible to use other buckles (not shown), instead of the buckle 16, so long as such buckles can sense a predetermined amount of tension and engage the strap 30 in response.

As a result of the locations and sizes of the areas of hook-bearing fastener material 54 and 58 and the loop-bearing fastener material 52 on the exterior face 50 of the strap 30, the portion 80 of the strap 30 extending outside the buckle 16 and being pulled by a person applying the pelvic sling 12 to an injured person is able to be securely held by the combination of hook-bearing fastener material and loop-bearing fastener material at any effective circumference of the pelvis stabilizing pelvic sling device 12 at which the pins 72 of the buckle 16 may be engaged in a pair of holes 40 along the strap 30. Thus, as shown in FIGS. 2, 3, and 4, with the effective circumference of the pelvic sling 12 at or near a minimum, the area of hook-bearing fastener material 58 aligned centrally along the second end portion 26 of the main body is engaged with a confronting portion of the loop-bearing fastener material 52 on the exterior side 50 of the strap 30. An available area of hook and loop fastener engagement is thus equal to the area of the hook-bearing fastener material 58 of one of the 3 strips shown in FIG. 1, and the mated fastener materials can hold the outer, or pulled end, portion 80 of the strap 30 securely enough to maintain enough tension in that portion 80 of the strap 30 so that the pins 72 of the buckle remain exposed beyond the sliding block 84 and engaged in the holes 40 of the strap 30.

In FIG. 8, the pelvis-stabilizing pelvic sling 12 is shown in tension as when in place on a person having a larger girth, and the loop-bearing fastener material 52 of the intermediate portion 38 of the strap 30 is not aligned with the area of hook-bearing fastener material 58. Instead, as shown in FIG. 8 the hook-bearing fastener material 54 mounted on the loop 36 of the outer end portion 34 is engaged with the loop-bearing fabric of the exterior layer 48 of the outer end portion 26 of the main body 14 on each side of the centrally located area of hook-bearing fastener material 58. As previously mentioned the fabric of the exterior layer 48 functions as loop-bearing fastener material. Accordingly, engagement of the area of hook-bearing fastener material 54 with the fabric 48 maintains sufficient tension in the outer, or pulled, portion 80 of the strap 30 to keep the pins 72 of the buckle 16 engaged in a pair of holes 40 in the strap 30, to maintain the proper amount of tension in the pelvic sling 12 to support and stabilize a person's fractured pelvis. It will be apparent that the loop 36 could be located slightly differently with the same position of the strap 30 with respect to the buckle, as shown in broken line. Thus the hook-bearing fastener material 54 could engage the fabric of the exterior layer 48 largely between two of the areas 58 of hook-bearing fastener material, overlapping somewhat on each of the areas 58, rather than by straddling a single area 58.

As shown in FIG. 9, with the pelvis-stabilizing pelvic sling 12 in place under proper tension on a somewhat larger person than in FIG. 8, the hook-bearing fastener material 54 on the loop 36 at the outer end 34 of the strap 30 may be engaged with loop-bearing fastener material 52 at the inner end 28 of the strap 30 where it is attached to the second end portion 26 of the main body 14 and may also be engaged with the fiber loops of the fabric of the exterior layer 48 of the outer end portion 26, to the extent that the area of hook-bearing fastener material 54 extends beyond the inner end portion 28 of the strap 30.

As may be seen in FIG. 10, with the pelvis-stabilizing pelvic sling 12 under the proper amount of tension to stabilize and support a fractured pelvis in an even larger person, the hook-bearing fastener material 54 on the loop 36 at the outer end of the strap 30 can mate securely with the loop-bearing fastener material 52 on the portion 74 of the strap 30 between the second end portion 26 of the main body 14 and the buckle 16. The mated hook-bearing fastener material 54 and loop-bearing fastener material 52 securely maintain sufficient tension in the strap 30 as it is engaged with the buckle 16 to keep the pins 72 engaged in a pair of holes 40 in the strap 30.

Thus by referring to FIGS. 4, 8, 9, and 10, it may be seen that, regardless of the circumference of the person on whom the device 12 is being used, within a relatively wide range of different circumferences, application of the device 12 is very straightforward. As a result of the availability and locations of the areas of flexible fastener material of two mating kinds, located on the second end portion 26 of the main body 14, on the strap 30, and on the loop 36, the outer, or pulled end, portion 80 of the strap 30 that extends beyond the buckle 16 can be fastened securely enough to maintain tension in the strap 30 to act against the sliding block 84 and thus maintain engagement of the buckle 16 with the pins 72 in any of the pairs of holes 40 along the part of the strap 30 extending beyond the second end portion 26 of the main body 14.

As the inner end portion 28 of the strap 30 is permanently attached to the second end portion 26 of the main body 14, adjustment of the pelvic sling 12 to provide the required amount of compression of the pelvis of an injured person is accomplished by pulling the strap 30 through the buckle 16, without first having to assemble any parts of the device. The pelvic sling 12 is placed around the hips of an injured person suspected of having a broken pelvis by sliding the main body portion 14 beneath the hips of the injured person. With the person lying in a supine position, the exterior side of the main body 14, the side shown in FIG. 1, should be downward. This permits the low friction plastic sheet 24 to slide easily along a surface of a backboard or other surface on which the person is resting, and exposes the necessary portions of the pelvic sling 12 so that it can be fastened.

Proper application of the pelvic sling 12 to an injured person thus can be accomplished simply and rapidly. First the sling should be placed at the level of the greater trochanters 66 and symphysis pubis, and the loop 36 and strap 30 must be passed through the opening in the frame 82 of the buckle 16 and around the curved face 87 of the sliding block 84. The pelvic sling can be tightened around a person by pulling the strap 30 and the buckle 16 in opposite directions, using the large loop 22 as a handle to pull toward the patient's left, as shown by the arrow 76, and, by using the large loop 36 as a handle, pulling the outer end 34 of the strap 30 in the opposite direction when the strap 30 extends through the buckle 16 and is doubled back toward the injured person's right side, as indicated by the arrow 78 in FIG. 2. The strap 30 is thus pulled through the buckle 16 until sufficient tension is achieved to move the sliding block 84 and allow the pins 72 to become engaged in a pair of holes 40 in the strap 30. While maintaining tension in the outer portion 80 of the strap 30 against the buckle 16, the flexible fastener materials can be engaged in one of the several alignments as described above to retain the tension in the strap 30 relative to the buckle 16 and thus to keep the pins 72 engaged in the holes 40 of the strap 30 at any effective circumference of the pelvic sling 12 at which the pins 72 are able to become engaged in a pair of holes 40.

Thus, engagement of the loop-bearing fastener material 52 of the strap 30 with the hook-bearing material in the areas 58 on the second end portion gives a first range of smallest available effective circumferences of the pelvic sling 12. Engagement of the fabric of the outer layer 48 of the second end portion of the main body 14 gives a second range of available, somewhat larger effective circumferences of the pelvic sling 12. Finally, engagement of the area 54 of hook-bearing fastener material of the outer end 34 of the strap with the loop-bearing fastener material 52 on the intermediate portion 38 of the strap 30 gives a third range of available effective circumferences, and the adjacent parts of the ranges overlap each other.

The pelvic sling 12 is made from a minimal number of components, and preferably of materials which are, except for the springs 90, radiolucent, and is ready for application as manufactured.

The pelvic sling 12 may be provided in various sizes. A normal size pelvic sling 12 may have a length of its main body length 98 of it main body of, for example, 24 inches, and larger and smaller sizes may be provided for use with very slender or very large persons. For a normal size pelvic sling 12 the length of the strap 30 combined with the extent of the loop 36 may be similar to or slightly shorter than the main body length 98.

While the description above has described the use of hook-bearing fastener material and loop-bearing fastener material, other two-component flexible fastener systems could also be used by similar placement of areas of the two matable fastener kinds on the strap 30 and a second end portion of a main body 14.

Referring next to FIGS. 11 and 11A, a pelvic sling 112 may also be used as a cervical support, hereinafter simply called a cervical collar, that can be wrapped around a patient's neck, as will be explained presently. The pelvic sling 112 is in many ways similar to the pelvic sling 12, and so like reference numbers will be used with like components of the pelvic sling 112. The pelvic sling 112 includes an inflatable bladder 114 in a central portion of the main body 14, where it may be located between two fabric layers 48 and 46. A fill tube 120 communicating with the bladder 114 may be provided on the outer side of the pelvic sling 112 at the first end portion 18 of the main body portion 14. A suitable fill fitting 122 may be provided on the fill tube 120 to permit temporary attachment of a squeeze bulb (not shown) or connection to another source of air to inflate the bladder 114. The fill fitting 122 may include a check-valve or other closure to maintain inflation of the bladder as required.

A piece of loop-bearing fastener material 123 may be provided on the second end portion 26 of the main body 14 as shown in FIG. 11, to supplement the loop-bearing nature of the fabric layer 48 if desired, to provide for secure engagement with the hook-bearing material 54 on the loop 36 at the outer end portion 34 of the strap 30.

A pair of elongate stays 124 and 126 are attached to the main body portion 14, as by strips 128 and 130 of strong fabric such as nylon webbing material sewn to the outer layer 48 of fabric of the main body portion 14. The strips 128 and 130 of fabric might also be attached by other means such as thermal welding or adhesives, if more practical. The stays 124 and 126 are spaced apart from each other along the length of the main body 14 and may reside near or even overlapping the respective opposite ends of the bladder 114, as may be seen in FIG. 11A. The stays 124 and 126 may be narrow and elongate, and are held where they extend transversely across the length of the main body 14, parallel with each other, where they can provide support along the opposite sides of a patient's neck when the pelvic sling 112 is utilized as a cervical collar, as will be explained in greater detail presently.

Each of the fabric strips 128 and 130 may thus have a length equal to the width of the main body portion 14 of the pelvic sling 112 and a width, parallel with the length of the main body 14 of, for example, about two inches. Each stay 124 and 126 may each have a length enough less than the width of the main body portion 14 to permit the opposite ends of the pieces of fabric 128 and 130 to be fastened securely to the main body 14 to capture the stays 124 and 126.

Each stay 124 or 126 may have a width of, for example, about 0.5 inch (1.25 mm), although the specific dimensions are not critical. Each of the stays 124, 126 may be made of a suitable metal with sufficient thickness to provide firm support for the main body 14. For example the stays 124, 126 may be of sheet steel or sheet aluminum, or a suitable composite material such as a fiber-reinforced resin of ample strength, with some amount of flexibility and resiliency.

It should be understood also that there might be only one, or more than two stays 124 and 126. Also, the stays might extend diagonally and might not be parallel with one another, in different embodiments of the pelvic sling, and might be wider and less elongate, or in the nature of small plates of metal. In one version such stays or plates might be malleable enough to be bent to a desired configuration to help support a patient's neck or pelvis.

An area 132 of flexible fastener material of the second kind, such as hook-bearing flexible fastener material, may be provided on the loop 36 at the outer end of the strap member 30, facing in the same direction as the inner side of the strap member 30, and thus opposite the hook-bearing material 54 on the outer end portion of the strap member 30, to be used to fasten the outer end 34 of the strap member 30 to the intermediate portion 38 of the strap member 30. The area 132 of fastener material may, as shown in broken line in FIG. 11, be an extension of the area of 54 of hook-bearing flexible fastener material with one part thereof located as described with respect to the separate piece 132 so as to be exposed on the inner side of the strap member 30 at its outer end 34.

A flexible tension-bearing member of another sort, such as a flexible cord, or cable, might also be attached to the second end portions 26 and used with a suitable fastener of a different sort, such as a spool or hook, (not shown) in place of the buckle 16 on the first end portion 18 of the main body portion 14, to hold the main body around a patient's fractured pelvis. Another sort of fastener (not shown) might then be used together with the flexible tension-bearing member to secure the elongate main body portion 14 wrapped around the neck of a patient P.

A pelvic sling 140 that can also be used as a cervical collar is shown in FIG. 12, but with only a short portion of the strap member 30. The pelvic sling 140 is similar in most respects to the pelvic sling 112, and so will be described in detail only with respect to the significant differences. The principal difference in the pelvic sling 140 is that it includes three separate bladders, each somewhat smaller than the bladder 114 as illustrated in FIGS. 11 and 11A. A central bladder 142 is the largest of the three and is located in substantially the same position, centrally within the main body portion 14, as the bladder 114 is in the previously described pelvic sling 112. Two more, smaller, bladders 144 and 146 are located respectively in the first end portion 18 and the second end portion 26. The bladders 142, 144, and 146 may all be installed in the same general manner as is the bladder 114 shown in FIGS. 11 and 11A, and respective fill tubes and fill fittings (not shown), may be utilized to inflate each of the bladders 142, 144, and 146, or the bladders may be interconnected with each other and inflated through a single fill tube. The stays 124 and 126 and their associated retaining fabric pieces 128 and 130 are, as shown in FIG. 12, located similarly to their locations as in the pelvic sling 112 shown in FIGS. 11 and 11A and are between the central bladder 142 and the respective one of the end bladders 144 and 146.

A pelvic sling 150 is yet another embodiment of the pelvic sling, as shown in FIG. 13. The pelvic sling 150 is generally similar to the pelvic sling 140 shown in FIG. 12, except that it lacks the stays 124 and 126 and their associated fabric strips 128 and 130, and, as a result, there is room for the central bladder 152 and respective end bladders 154 and 156 to be somewhat larger and extend toward each other slightly more closely than the similar locations of the bladders 142, 144, and 146 of the sling 140. The bladders 142, 144, and 146 may be inflated when the pelvic sling 112 or 140 is used, taking care not to provide too much tension in the pelvic sling.

Figure 14:
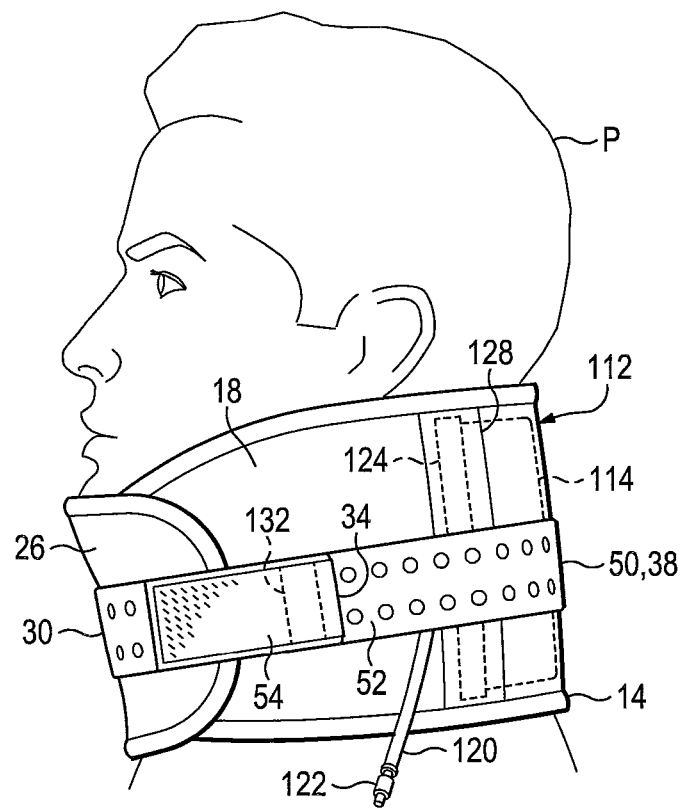
FIG. 14 is a perspective view showing the pelvis-stabilizing device shown in FIGS. 11 and 11A in use as a cervical collar to support a person's neck.

Referring next to FIG. 14, the pelvic sling 112 is shown as used as a cervical collar on a patient P. For use of the pelvic sling 112 as a cervical collar, the main body portion 14 is wrapped around the neck of the patient P. The device 112 is placed around the neck of the patient P with the buckle 116 extending beyond the first end 18 of the main body portion and toward the posterior of the patient on the patient's right hand side. The strap member 30 is extended around the main body portion and overlapped onto its own intermediate portion 38, and the outer end 34 of the strap member 30 is fastened to the intermediate portion 38 by mating interaction between the two types of fastener material. Thus when using the Velcro™ type hook and loop fastening materials described above, the piece of hook-bearing fastener material 132 on the outer end 34 of the strap member 30 mates securely with the loop-bearing fastener material 52 on the exterior side 50 of the intermediate portion 38 of the strap member 30. The second end portion 26 of the main body portion 14 of the pelvic sling 112 overlaps the first end portion 18 and can be positioned by the medical service provider applying the device 112 as a cervical collar to provide the needed support for the chin of the patient P. With the device ideally located the stays 124 and 126 extend vertically along the neck of the patient P, providing stiffness in a lateral direction with respect to the main body portion 14, that is, generally vertically along the neck of the patient P as shown in FIG. 14. Medical personnel can, if necessary, bend one or both of the stays 124, 126 to conform as desired to the patient's shoulders, neck, and head, and the device 112 can be placed on the neck of the patient P in the location deemed most appropriate to place the stays 124 and 126 where required, which may ordinarily be in a generally symmetrical arrangement with the stay 124 near the patient's left ear or jaw and the stay 126 near the patient's right ear or jaw. With the device wrapped around the neck of the patient P and the outer end 34 of the strap member 30 secured to the intermediate portion 38 of the strap 30 as shown in FIG. 14, the bladder 114 may be inflated as desired to provide support and to cause the interior layer 46 of fabric of the main body portion 14 to conform to and press against the neck of the patient P with a desired amount of pressure, by adjusting the extent of inflation of the bladder 114. Either the pelvic sling 140 or the pelvic sling 150 would also be applied to the support the neck of a patient P in the same manner shown in FIG. 14, with the exception of additionally having the optional use of the additional bladders 144, 146, 154, and 156 to modify the amount of support provided to the neck of patient P, and that in application of the pelvic sling 150 as a cervical collar the stays 124 and 126 are not available to provide support for the neck of the patient P as with the pelvic slings 112, and 140.

Figure 15:
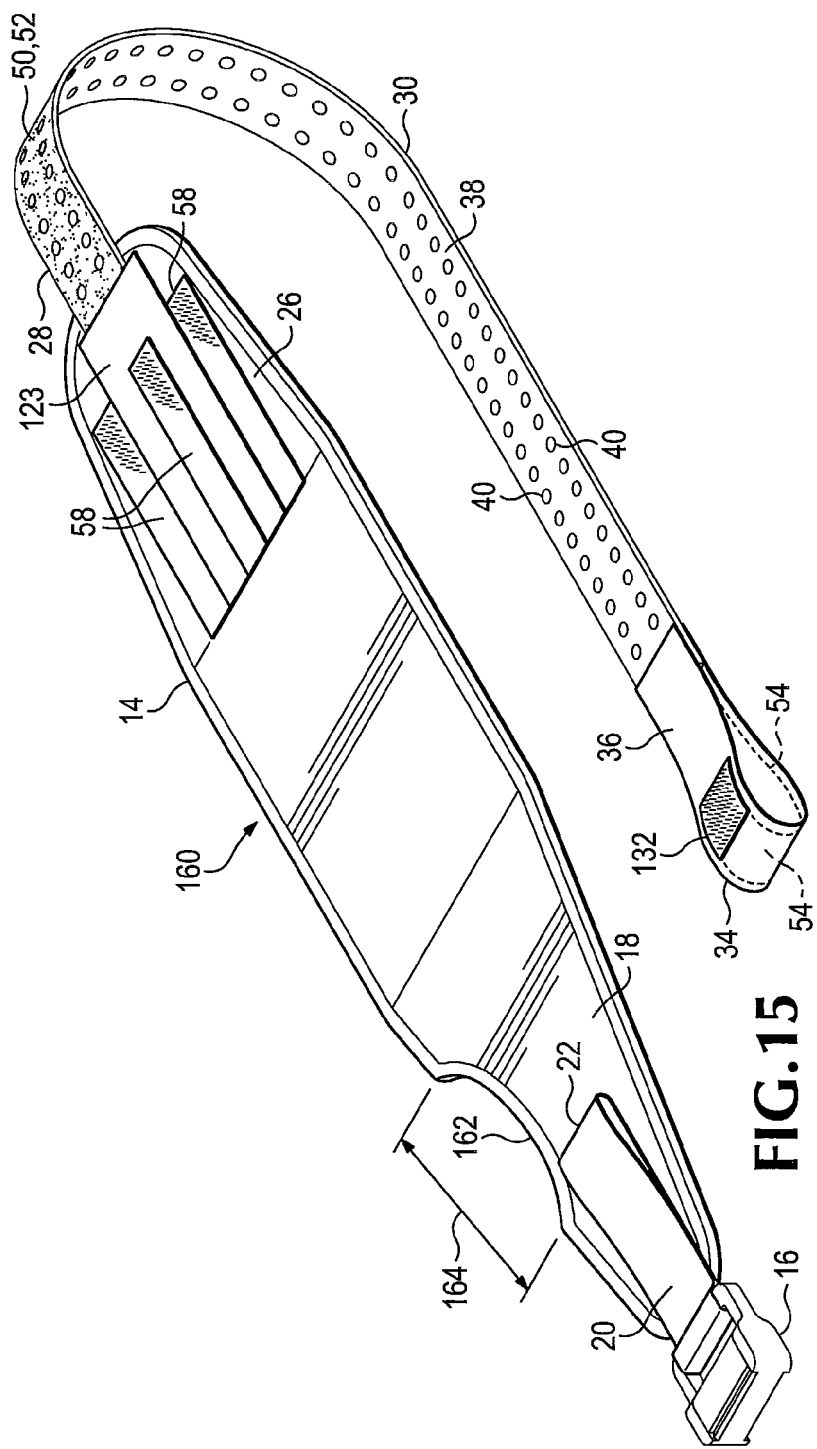
FIG. 15 is a perspective view of a pelvis-stabilizing device which is yet another alternative embodiment of the device shown in FIGS. 1-10, which may also be used as a cervical collar to support a person's neck.
Figure 16:
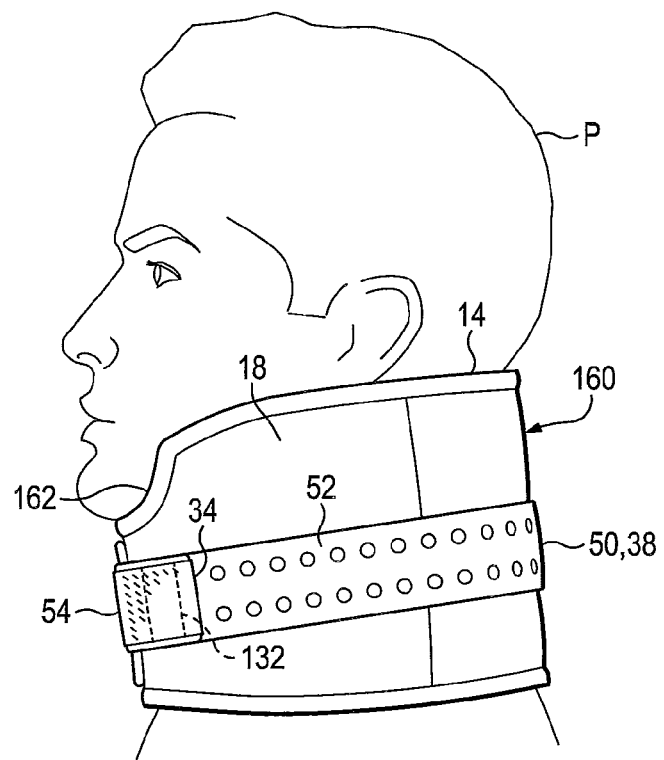
FIG. 16 is a perspective view of the pelvis-stabilizing device shown in FIG. 15 in use as a cervical collar to support a person's neck.

Referring next to FIGS. 15 and 16, a pelvic sling 160 is yet another embodiment of the pelvic sling shown in FIGS. 1-10 and is generally similar to the pelvic sling 12 except as will be described presently. The pelvic sling 160 is shown including a piece 123 of loop-bearing fastener material attached to the second end portion 126 of the main body portion 14. As with the pelvic slings 112, 140, and 150, an area of hook-bearing flexible fastener material 132 is attached to the interior side of the strap member 30 at its outer end 34.

On one side of the first end portion 18 a margin is shaped to define a concave-shaped chin receptacle part 162 spanning a distance 164 of several inches of the main body portion 14 of the pelvic sling 160 for use of the pelvic sling 160 as a cervical collar as shown in FIG. 16. The distance 164 may, for example, be in the range of 4-8 inches and more preferably in the range of about 5-7 inches when the pelvic sling 160 is straightened out into a flat condition as shown in FIG. 15. While an arcuate concave chin receptacle 162 is shown the shape may vary, so long as there is some concavity and opposite sides to receive and help to stabilize the chin of the patient P.

For the sake of simplicity, the pelvic sling 160 is shown in FIGS. 15 and 16 with the simple construction of the main body portion 14 similar to that shown in FIGS. 1-10, without showing any bladders or stays. It will be understood that in another embodiment including the concave margin defining the chin receptacle 162, one or more bladders might be included as shown in FIGS. 11, 11A, 12, and 13. Similarly, stays 124 and 126 might be included in the pelvic sling 160.

When the pelvic sling 160 is used as a cervical collar, as shown in FIG. 16, it can be placed under the chin of a patient P as shown in FIG. 16 to receive and assist in stabilizing the chin of the patient P as the body portion 14 is wrapped around the neck of the patient P and the outer end 34 of the strap member 30 is connected to the intermediate portion 38 of the strap member 30 by interaction of the hook-bearing fastener material in the area 132 with the loop-bearing fastener material 52 on the exterior side 50 of the intermediate portion 38 of the strap member 30, as shown in FIG. 16.

Figure 17:
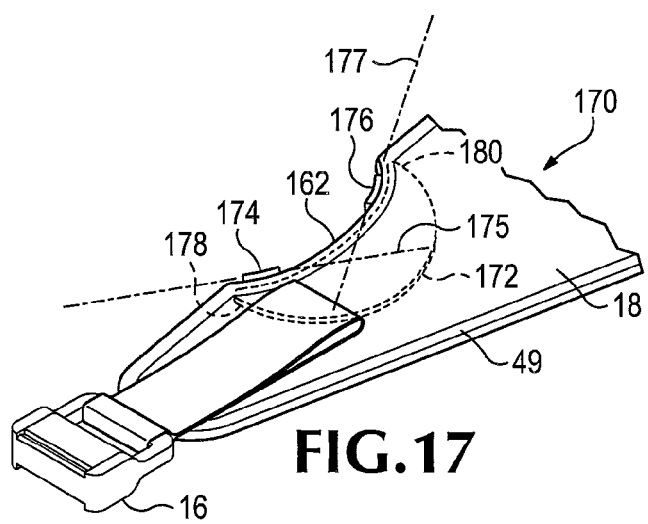
FIG. 17 is a view of an end portion of the main body of a pelvis-stabilizing and neck-supporting device similar to that shown in FIG. 15 and incorporating a chin rest, shown in a non-deployed position with respect to the body portion of the pelvis-stabilizing and neck supporting device.
Figure 18:
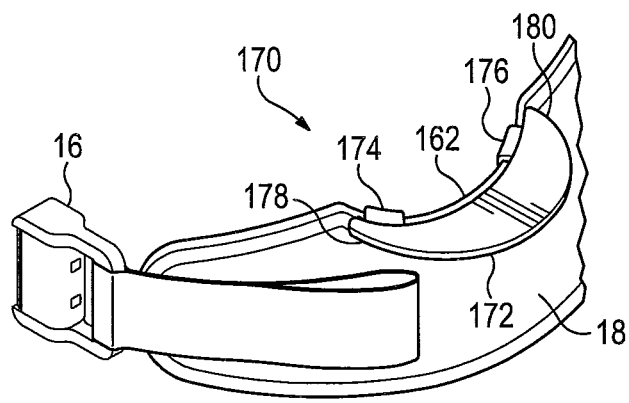
FIG. 18 is a view similar to FIG. 17, showing the chin rest in a deployed position.
Figure 19:
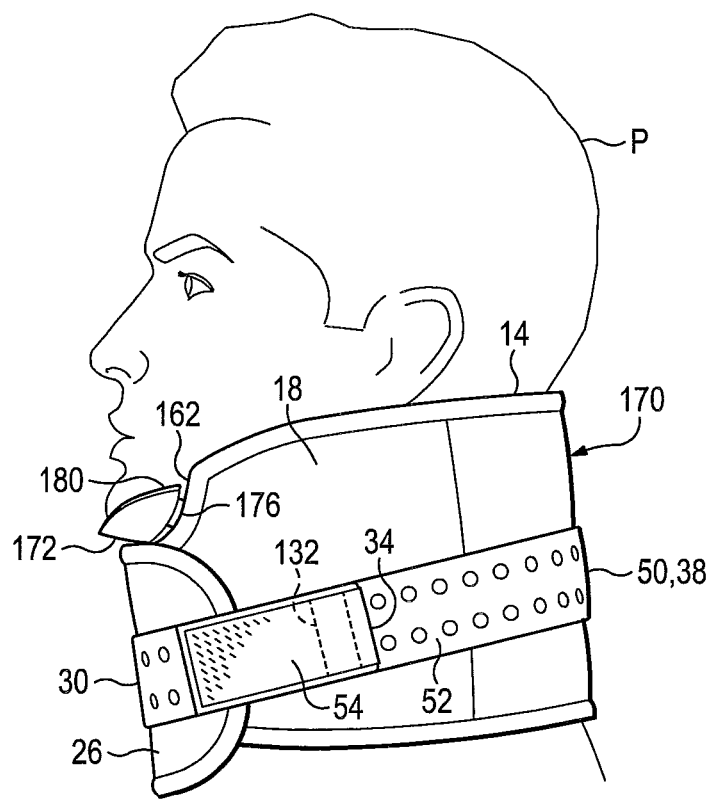
FIG. 19 is a perspective view of the pelvis-stabilizing and neck supporting device shown in FIGS. 17 and 18 in use as a cervical collar to support a person's neck.

A pelvic sling 170, shown in FIGS. 17-19, is similar to the pelvic sling 160 shown in FIGS. 15 and 16, except with respect to its first end portion 18, where there is a moveable chin support piece 172 attached to the margin of the outer end portion 18 and aligned with the concave chin receptacle portion 162 of the margin of the outer end portion 18. As shown in FIG. 17, the outer end portion 18 is flat, as in FIG. 15, and the movable chin support piece 172 is in a retracted, or non-deployed, position lying closely alongside the interior face of the main body portion 14 of the pelvic sling 170. The moveable chin support piece 172 is attached to the margin of the end portion 18 by a pair of hinges 174 and 176 located near the opposite ends 178 and 180 of the moveable chin support piece 172. The hinges 174 and 176 have respective hinge axes 175 and 177 aligned with the locations on the concave chin rest margin portion 162 where each hinge is attached and interconnects the end portion 18 with the moveable chin support piece, and as a result the axes 175 and 177 of the hinges 174 and 176 are coplanar but not parallel, and diverge from each other by an obtuse angle, as seen in FIG. 17, when the end portion 18 lies flat.

The moveable chin support piece 172 may be of a somewhat stiff and self-supporting yet flexible material such as multiple layers of heavy laminated textile fabric, or a somewhat flexible yet fairly stiff synthetic plastics material, so that the moveable chin support piece is able to flex along with the end portion 18 and lie closely alongside it when the pelvic sling 170 incorporating such a moveable chin support piece 172 is applied as a pelvic sling with the moveable chin support piece 172 in the retracted, non-deployed position shown in FIG. 17. The hinges 174 and 176 may be, for example, short pieces of narrow strong textile fabric such as nylon webbing sewn to the concave portion 162 of the margin of the end portion 18 and to the concave inner margin of the moveable chin support piece 172. Alternatively, particularly if the moveable chin support piece 172 is of molded plastics material, the hinges 174 and 176 may be "live" plastic hinges with connected ears that can be sewn or otherwise fastened in well-known ways to the material of the outer end portion 18 and the chin support piece 172. Also instead of being permanently attached and moveable, the chin support piece 172 could be attached to the end portion 18 of the main body portion 14 by detachable fasteners, such as Velcro, snap fasteners, or buttons.

When it is desired to use the pelvic sling 170 as a cervical collar, the moveable chin support piece 172 can be deployed to the exterior side of the end portion 18. With the end portion 18 bent as shown in FIGS. 18 and 19 so as to fit around and conform to the neck of a patient P, the axes of rotation of the hinges 174 and 176 are no longer coplanar, but are oriented differently with respect to each other, so that the moveable chin support piece 172 is held in a nearly horizontal orientation extending outwardly from the outer end portion 18 with an upwardly concave curved shape, so that it can support and cradle the chin of the patient P as shown in FIG. 19. Thus when the pelvic sling 170 is used as a cervical collar as shown in FIG. 19 the moveable chin support piece 172 is deployed, and the main body portion 14 is placed on the neck of the patient P so it can support and cradle the chin of the patient P. The second end portion 26 of the pelvic sling 170, depending upon the size and circumference of the neck of the patient P, may provide more or less additional support beneath the moveable chin support piece 172, with the outer end 34 of the strap member 30 secured to the intermediate portion 38 of the strap member 30 by interaction between the area 132 of hook-bearing fastener material on the outer end 34 of the strap member with the loop-bearing fastener material 52 on the intermediate portion 38 of the strap member 30.

It will be understood that the main body portion 14 of the pelvic sling 170 might be constructed in any desired one of the various configurations shown in FIGS. 1-13, to include or not to include one or more inflatable bladders and transversely-oriented stays while still incorporating the moveable chin support piece 172.

Depending upon whether it is desired for the pelvic sling 170 to be able to be used only once or for more or fewer patients P, it will be understood that the moveable chin support piece 172 may also be made of various materials such as plastics, impregnated cloth or laminated paper, for example.

The terms and expressions which have been employed in the foregoing specification arc used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A device useful alternatively for stabilizing a fractured pelvis or as a cervical collar for supporting a neck, comprising:
   (a) an elongate main body portion having opposite first and second end portions;
   (b) a buckle fixedly attached to said first end portion of said main body portion;
   (c) a flexible elongate strap having an inner end fixedly attached to said second end portion of said main body portion, the strap extending away from the main body portion and having an outer end portion opposite from said inner end thereof, the strap being of a size able to pass through the buckle and the buckle being adapted to engage the strap so as to interconnect the first and second end portions of the main body portion with each other, for use of the device in stabilizing a pelvis, and the strap having an intermediate portion, located between the outer end portion of the strap and the second end portion of the main body portion, having an area of flexible fastener material of a first kind located on a first side of the strap and having an area of flexible fastener material of a second kind that is cooperatively matable with the flexible fastener material of the first kind, located on a second side of the outer end portion of the strap, the area of flexible fastener material of the second kind being capable of fastening the outer end portion of the strap to the intermediate portion of the strap by mating with the flexible fastener material of the first kind, to secure the device as a cervical collar with the main body portion wrapped around a person's neck and with the strap extending further around the main body portion.

2. The device of claim 1, wherein said first end portion of said main body portion has a margin that defines a concave chin receptacle, and further including a movable chin support member attached to said first end portion of main body portion adjacent said chin receptacle, said chin support member being optionally positioned with respect to said main body portion either in a chin-supporting deployed configuration projecting outward from said main body portion when said main body portion is bent to extend around a neck of a patient, or in a non-deployed position alongside and generally parallel with said main body portion.

3. The device of claim 2 wherein said chin support member has a pair of opposite ends each attached to said main body portion through a separate respective hinge, each of the hinges defining a respective hinge axis, the hinge axes being coplanar and intersecting each other at an obtuse angle when said first one of said end portions of said main body portion is in a flattened generally planar condition.

4. The device of claim 1 further including a selectively inflatable bladder located centrally in said main body portion between said opposite first and second end portions thereof.

5. The device of claim 1 further including a pair of elongate stays each having a longitudinal axis, mounted on said main body portion at respective spaced-apart positions, the stays being oriented transversely to a length of said main body portion and with their longitudinal axes parallel with each other.

6. The device of claim 1 wherein said stays are located adjacent respective opposite ends of said inflatable bladder.

7. The device of claim 1 including at least one additional selectively inflatable bladder located in a respective one of said end portions of said main body portion.

8. A device useful alternatively for stabilizing a fractured pelvis or as a cervical collar for supporting an injured neck, comprising:
(a) an elongate main body portion having opposite first and second end portions;
(b) a buckle fixedly attached to said first end portion of said main body portion;
(c) a flexible elongate strap having an inner end fixedly attached to said second end portion of said main body portion, the strap extending away from the main body portion and having an outer end portion opposite from said inner end thereof, the strap being of a size to pass through the buckle and the buckle being adapted to engage the strap so as to interconnect the first and second end portions of the main body portion with each other, and an intermediate portion of the strap, located between the outer end portion of the strap and the second end portion of the main body portion, having an area of flexible fastener material of a first kind located on a first side of the strap;
(d) an area of flexible fastener material of a second kind that is cooperatively mateable with the flexible fastener material of the first kind, located on the outer end portion of the strap;
(e) an area of flexible fastener material of the first kind located in the second end portion of the main body portion where the outer end portion of the strap can be fastened to the second end portion of the main body portion by mating cooperation of the respective areas of flexible fastener material of the first and second kinds, when the device is adjusted to a circumference in a predetermined first range of circumferences;
(f) an area of flexible fastener material of the second kind, located on the second end portion of the main body portion adjacent the area of flexible fastener material of the first kind, where the intermediate portion of the strap can be fastened to the second end portion of the main body portion by mating cooperation of the flexible fastener material of the first kind located on the intermediate portion of the strap with the flexible fastener material of the second kind located on the second end portion of the main body portion when the device is adjusted to a circumference in a range of circumferences smaller than said first range of circumferences; and wherein
(g) said first one of said end portions of said main body portion has a margin that defines a concave chin receptacle.

9. A device useful alternatively for stabilizing a fractured pelvis or as a cervical collar for supporting an injured neck, comprising:
(a) an elongate main body portion having opposite first and second end portions;
(b) a buckle fixedly attached to said first end portion of said main body portion;
(c) a flexible elongate strap having an inner end fixedly fastened to said second end portion of said main body portion, the strap extending away from the main body portion and having an outer end portion opposite from said inner end thereof, the strap being of a size to pass through the buckle and the buckle being adapted to engage the strap so as to interconnect the first and second end portions of the main body portion with each other, and an intermediate portion of the strap, located between the outer end portion of the strap and the second end portion of the main body portion, having an area of flexible fastener material of a first kind located on a first side of the strap;
(d) an area of flexible fastener material of a second kind that is cooperatively mateable with the flexible fastener material of the first kind, located on the outer end portion of the strap;
(e) an area of flexible fastener material of the first kind located in the second end portion of the main body portion where the outer end portion of the strap can be fastened to the second end portion of the main body portion by mating cooperation of the respective areas of flexible fastener material of the first and second kinds, when the device is adjusted to a circumference in a predetermined first range of circumferences;
(f) an area of flexible fastener material of the second kind, located on the second end portion of the main body portion adjacent the area of flexible fastener material of the first kind, where the intermediate portion of the strap can be fastened to the second end portion of the main body portion by mating cooperation of the flexible fastener material of the first kind located on the intermediate portion of the strap with the flexible fastener material of the second kind located on the second end portion of the main body portion when the device is adjusted to a circumference in a range of circumferences smaller than said first range of circumferences; and
(g) a selectively inflatable bladder located centrally in said main body portion between said opposite first and second end portions thereof.

10. A device for stabilizing a fractured pelvis, comprising:
(a) an elongate main body portion having opposite first and second end portions;
(b) a buckle fixedly attached to said first end portion of said main body portion;

(c) a flexible elongate strap having an inner end permanently attached to said second end portion of said main body portion, the strap extending away from the main body portion and having an outer end portion opposite from said inner end thereof, the strap being of a size to pass through the buckle and the buckle being adapted to engage the strap so as to interconnect the first and second end portions of the main body portion with each other;

(d) an area of a first kind of flexible fastener material on said second end portion of said main body portion;

(e) an area of flexible fastener material of a second kind that is cooperatively mateable with the flexible fastener material of the first kind, located on the outer end portion of the strap;

(f) an area of flexible fastener material of the first kind located in the second end portion of the main body portion where the outer end portion of the strap can be fastened to the second end portion of the main body portion by mating cooperation of the respective areas of flexible fastener material of the first and second kinds, when the device is adjusted to a circumference in a predetermined first range of circumferences; and (g) a pair of elongate stays mounted on said main body portion at respective spaced-apart positions, the stays being oriented parallel with each other and transversely to a length of said main body portion.

* * * * *